United States Patent [19]
Hortin et al.

[11] Patent Number: 6,129,912
[45] Date of Patent: Oct. 10, 2000

[54] POLYETHYLENE GLYCOL-PROTEIN COMPOSITIONS WHICH REDUCE THE ANTIGENIC DISPLAY OF RED BLOOD CELLS

[75] Inventors: Glen L. Hortin, North Potomac, Md.; Shu T. Huang, Birmingham, Ala.

[73] Assignee: UAB Research Foundation, Birmingham, Ala.

[21] Appl. No.: 09/160,013

[22] Filed: Sep. 24, 1998

Related U.S. Application Data

[60] Provisional application No. 60/060,235, Sep. 26, 1997.

[51] Int. Cl.⁷ .............................. A01N 1/02; A61K 35/18; C12N 5/06
[52] U.S. Cl. .................... 424/93.73; 424/93.1; 424/93.7; 435/1.1; 435/2; 435/325; 435/372
[58] Field of Search .............................. 424/93.73, 93.1, 424/93.7, 93.71; 525/54.11; 435/1.1, 2, 325, 372, 374

[56] References Cited

U.S. PATENT DOCUMENTS 5,498,421  3/1996  Grinstaff et al. ........................ 424/450
5,908,624  6/1999  Scott et al. .............................. 424/93.7

OTHER PUBLICATIONS

Murad, K. et al. Molecular camoflage of antigenic determinants on intact mammalian cell: Possible applications to transfusion medicine. Blood v 88 #10 Suppl 1, p. 444a, Abstract 1765, Nov. 15, 1996.

Monfardini, et al. A branched monomethoxypoly(ethylene glycol) for protein modification. Bioconjugate Chemistry. v6 #1, pp. 62–69, Feb. 13, 1995.

*Primary Examiner*—David Saunders
*Attorney, Agent, or Firm*—Benjamin Aaron Alder

[57] ABSTRACT

The present invention provides a composition of matter, comprising a red blood cell coated a polymeric mixture of polyethylene glycol and albumin. Also provided is a method of blocking blood group antigens on the surface of a red blood cell, comprising the step of contacting said cell with a pharmacologically effective concentration of the composition of the present invention.

19 Claims, 5 Drawing Sheets

6,129,912

POLYETHYLENE GLYCOL-PROTEIN COMPOSITIONS WHICH REDUCE THE ANTIGENIC DISPLAY OF RED BLOOD CELLS

CROSS-REFERENCE TO RELATED APPLICATION

This non-provisional patent application claims benefit of provisional patent application U.S. Ser. No. 60/060,235, filed Sep. 26, 1997, now abandoned.

BACKGROUND OF THE INVENTION

1. Field of the Invention

The present invention relates generally to the fields of molecular biology and erythrocyte biochemistry. More specifically, the present invention relates to reduced antigenic cells and uses therefor.

2. Description of the Related Art

Many polymorphic blood group antigens are expressed on the surface of human red blood cells (Issitt 1985; Mollison, Engelfriet, and Contreras 1987). These include the well-known ABO type and Rh antigen (also termed D antigen) as well as many other less familiar antigens. As a consequence of the antigenic diversity of red cells, it is not possible to transfuse blood that is antigenically identical with a recipient, unless blood is provided by autologous donation or by an identical twin. Recipients of multiple transfusions develop antibodies against the nonself antigens on red cells.

Alloimmunization also can occur during pregnancy if there is fetal-maternal exchange of blood. As antibodies to other individuals' red cell antigens develop, it becomes progressively harder to provide compatible blood and to avoid transfusion reactions. Transfusion of compatible blood also becomes impossible in patients with autoimmune disorders who produce antibodies against antigens of their own red blood cells. The red cells in individuals with autoimmune disorders and any transfused red cells are destroyed, producing an autoimmune hemolytic anemia which can be fatal in severe cases.

The prior art is deficient in the lack of effective means of producing red cells that are compatible with all recipients and in the lack of reduced antigenic cells and uses therefor. The present invention fulfills this longstanding need and desire in the art.

SUMMARY OF THE INVENTION

Cell antigens, such as red cell antigens can be masked with a nonantigenic polymer, polyethylene glycol (PEG), as a means of producing red cells compatible with all recipients, including those with multiple alloantibodies or autoantibodies to red cells. In previous studies, the technique of covalently coupling polyethylene glycol (PEG) derivatives to the surface of red cells as a means of covering blood group antigens and producing cells that could serve as universal donor cells for transfusion was described. Effective blockade of red cell antigens was achieved with activated esters of polyethylene glycol.

The present invention involves a second generation technique which is an improved procedure in which multiple layers of polyethylene glycol-albumin copolymers are generated instead of a single layer of individual polyethylene glycol polymer on the red cell surface. This new technique showed less red cell damage and was much more efficient in blocking red cell antigen-antibody reactions. Survival studies of treated mouse red blood cells showed a normal 27 day red blood cell life span similar to untreated mouse red cells. This new technique offers the potential for universal donor red cells for blood transfusion.

In one embodiment of the present invention, there is provided a composition of matter, comprising a red blood cell coated a polymeric mixture of polyethylene glycol and albumin.

In yet another embodiment of the present invention, there is provided a method of blocking blood group antigens on the surface of a red blood cell, comprising the step of contacting said cell with a pharmacologically effective concentration of the composition of the present invention.

In yet another embodiment of the present invention, there is provided a composition of matter, comprising a cell coated with a cross-linked or branched polyethylene glycol and a protein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows that 40% of control untreated mouse red blood cells and 60% of the treated mouse red blood cells were rapidly cleared within one day. These represent a fraction of damaged red cells after one week storage in AS-5 additive solution that was rapidly cleared. AS-5 additive solution is designed to preserve human red blood cells and may not be optimal for mouse red blood cells. The remaining red blood cells one day after transfusion showed similar survival curves when compared to untreated red blood cells.

DETAILED DESCRIPTION OF THE INVENTION

Figure 1:
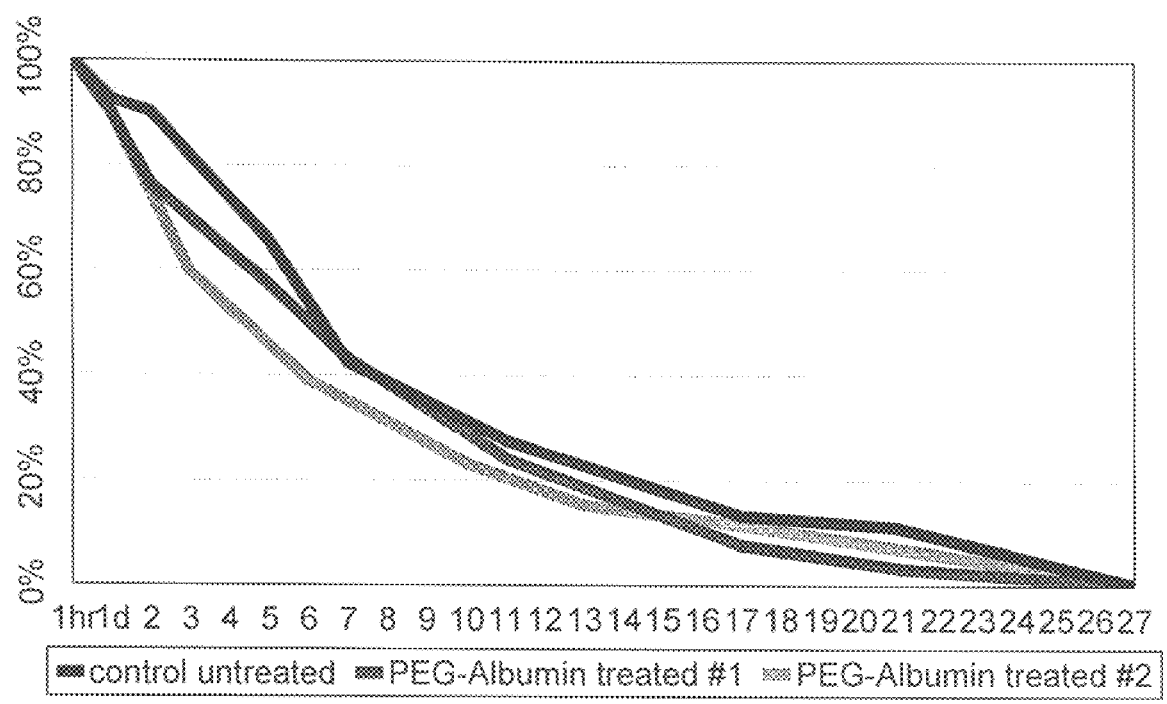
FIG. 1 shows that polyethylene glycol-albumin polymer treated mouse red blood cells have the same survival over 27 days as untreated mouse red blood cells.

In the present invention, coupling of an inert polymer to the surface of red cells was examined as a means of covering blood group antigens and producing cells that could serve as universal donor cells for transfusion. Effective blockade of red blood cell antigens was achieved with N-hydroxysuccinimide-activated esters of polyethylene glycol. It was possible to block all antigens tested, but lower concentrations of reactants were required to block peptide-defined antigens than carbohydrate-defined antigens. Red cells remained intact after modification but were significantly damaged. The present invention demonstrates the feasibility of antigenic blockade of red cells and that damage can be reduced during coupling reactions to produce viable red cells.

The present invention is directed to a composition of matter, comprising a red blood cell coated with an inert, nonantigenic polymer. Preferably, the polymer is a N-hydroxysuccinimide-activated ester of polyethylene glycol. The polymer may be a bis(propionyl-N-hydroxysuccinimide)-polyethylene glycol. Alternatively, the polymer is propionyl-N-hydroxysuccinimide-methoxypolyethylene glycol with a molecular weight of 5,000. Preferably, the red blood cell coated with an inert, nonantigenic polymer has been treated with a concentration of about 1% of the polymer.

The present invention is also directed to a method of blocking blood group antigens on the surface of a red blood cell, comprising the step of contacting said cell with a pharmacologically effective concentration of the composition of the present invention. Preferably, the blocking of the blood group antigens on the surface of the cell significantly reduces the antigenicity of such red blood cells when administered to an individual in need of such treatment. Preferably, the polymer is a N-hydroxysuccinimide-activated ester of polyethylene glycol. The polymer may be a bis(propionyl-N-hydroxysuccinimide)-polyethylene glycol. Alternatively, the polymer is propionyl-N-hydroxysuccinimide-methoxypolyethylene glycol with a molecular weight of 5,000. Preferably, the red blood cell coated with an inert, nonantigenic polymer has been treated with a concentration of about 1% of the polymer.

Many polymorphic blood group antigens are expressed on the surface of human red blood cells (Issitt 1985; Mollison, Engelfriet, and Contreras 1987). These include the well-known ABO type and Rh antigen (also termed D antigen) as well as many other less familiar antigens. As a consequence of the antigenic diversity of red cells, it is not possible to transfuse blood that is antigenically identical with a recipient, unless blood is provided by autologous donation or by an identical twin. Recipients of multiple transfusions develop antibodies against the nonself antigens on red cells. Alloimmunization also can occur during pregnancy if there is fetal-maternal exchange of blood. As antibodies to other individuals' red cell antigens develop it becomes progressively harder to provide compatible blood and to avoid transfusion reactions. Transfusion of compatible blood also becomes impossible in patients with autoimmune disorders who produce antibodies against antigens of their own red blood cells. Their own red cells and any transfused red cells are destroyed, producing an autoimmune hemolytic anemia which can be fatal in severe cases. It is also important to note that not all antigens need to be blocked on each cell for the present compositions to have utility. For example, one may only block Rh determinant on cells which could be useful for autoimmune hemolytic problems.

The masking of red cell antigens with a nonantigenic polymer, polyethylene glycol (PEG), as a means of producing red cells compatible with all recipients, including those with multiple alloantibodies or autoantibodies to red cells is shown herein. The first generation technique which conjugated polyethylene glycol polymer to the red cell surface to decrease red cell agglutination showed only partial blockage of red cell antigen-antibody reaction and moderate damage of red cell membrane. Significant reduction in red cell damage resulted from use of a group of polyethylene glycol reagents that were of higher molecular weight. However, blockade of antigens were still incomplete.

The present invention shows the development of a second generation improved technique which conjugates a small amount of polyethylene glycol-albumin copolymers on the red cell surface first with subsequent deposition of layer by layer of polyethylene glycol-albumin copolymers on top of the existing polymers on red cell surface. This new technique showed that all of the red cell antibodies could be completely blocked, except ABO antibodies which showed very weak microscopic reactions. Developing layers of cross-linked PEG-albumin copolymers to cover the red cell surface is much thicker and much more efficient in covering the red cell antigens than polyethylene glycol polymer alone. Also, these new polyethylene glycol-albumin copolymers have less attached points on red cell surface, therefore causing less damage to the red cells. This technique can be used to create universal donor red cells for blood transfusion, since it showed efficient blockade of red cell antigen-antibody reaction while preserving normal red cell morphology and red cell survival.

Thus, the present invention relates to a composition of matter, comprising a red blood cell coated a polymeric mixture of polyethylene glycol and albumin. Generally, any protein or compound containing multiple reaction sites with activated esters which form a cross-linked matrix can be used to create the universal donor blood cells of the present invention. Preferably, the concentration of the polyethylene glycol is from about 0.5% to about 1.0%. In addition, the preferable concentration of the albumin is from about 1.25% to about 2.5%. Representative examples of suitable albumin formulations include ALBUMARC™ 5% albumin from the American Red Cross Blood Services and ALBUTEIN™ 5% albumin from the Alpha Therapeutic Corporation. Preferably, the cell is coated with the polymeric mixture during one single reaction although multiple treatments could be applied.

The present invention relates to a method of blocking blood group antigens on the surface of a red blood cell, comprising the step of contacting said cell with a pharmacologically effective concentration of the composition disclosed herein. Preferably, the concentration of the polyethylene glycol is from about 0.5% to about 1.0%. In addition, the preferable concentration of the albumin is from about 1.25% to about 2.5%. Representative examples of suitable albumin formulations include ALBUMARC™ 5% albumin from the American Red Cross Blood Services and ALBUTEN™ 5% albumin from the Alpha Therapeutic Corporation. Preferably, the cell is coated with a polymeric mixture one time so as to allow the interactive polyethylene glycol and albumin copolymer to develop thicker and thicker polymers on the red cell surface. This procedure can be repeated if necessary.

The following examples are given for the purpose of illustrating various embodiments of the invention and are not meant to limit the present invention in any fashion.

EXAMPLE 1

Materials and Methods

Polyethylene glycol (PEG) derivatives were purchased from Shearwater Polymers (Huntsville, Ala.). Red blood cells were obtained from segments attached to units of donor red blood cells. Imucor (Norcross, Ga.) was the source of monoclonal/polyclonal anti-human globulin, antibodies to human red cell antigens. Fresh porcine blood was obtained from the Animal Care Facility. Lectins were purchased from Gamma Biologicals (Houston, Tex.). Red blood cell bound antibody was measured by the UAB Immunecytopenia Laboratory using an immunoassay as previously described by LoBuglio et al (1983). Agglutination reactions of red cells were assayed by standard tube techniques as described by the Technical Manual for blood banks (Walker et al., 1990). Quantitative estimates of the strength of agglutination reactions were made after serial dilution of the agglutinating serum. Strength of agglutination is expressed as titer scores which relates to the inverse of the dilution yielding agglutination.

Coupling of activated polyethylene glycols to red blood cells was conducted in 140 mM NaCl, 20 mM N-[2-hydroxyethyl)piperazine-N'[2-ethanesulfonic acid] (HEPES) adjusted to pH 8.0. A 5% suspension of red blood cells was mixed at 4° C. with activated polyethylene glycol derivatives added to varying percentages by weight. Incubations were at 4° C. overnight. Cells were washed in a centrifugal cell washer before any analysis.

EXAMPLE 2

Results

Incubation of red cells overnight with the bifunctional activated polyethylene glycol derivative, bis(propionyl-N-hydroxysuccinimide)-polyethylene glycol of 3,400 daltons progressively blocked agglutination reactions by antibodies to blood group antigens such as A, A'B, and D antigens as the concentration of reagent was increased (TABLE I). The D antigen, which is one of the polypeptide-defined determinants of the Rh system, was blocked at a lower concentration than required for antigenic determinants defined by carbohydrate groups, e.g., the very high concentration of reagent required to block the A and A'B antigens. It was difficult to achieve 100% blockade of agglutination against these high abundance, carbohydrate-defined blood group antigens. Preferential blockade of polypeptide-defined antigens is not surprising considering the preferential reactivity of the active carboxy esters with amino rather than hydroxyl groups (Zalipsky and Lee 1992). Polypeptides may be preferred sites of covalent coupling of the activated polyethylene glycols on the surface of red cells.

TABLE I

Blockade of blood group antigens by coupling with bis(propionyl-N-hydroxysuccinimide)-polyethylene glycol of 3,400 daltons Titer Scores for Agglutination of Red Cells

| % PEG | Anti-A | Anti A'B | Anti-D |
|---|---|---|---|
| 0 | 2048 | 1024 | 256 |
| 10 | 2048 | 1024 | 0 |
| 20 | 1024 | 512 | 0 |
| 30 | 32 | 64 | 0 |
| 40 | 16 | 16 | 0 |
| 50 | 2 | 4 | 0 |

Agglutination reactions of polyethylene glycol-modified red cells bearing the A, A'B, and D antigens with serial dilutions of antisera versus the respective antigens were examined.

EXAMPLE 3

It was expected that use of a reagent with a large molecular size would prevent entry of the reagent into cells and would minimize modification or damage to internal components of cells. There was a limited amount of hemolysis of cells, and there was little change in the size distribution of red cells when analyzed with an electronic hematology analyzer. However, cells did undergo some damage as evident by more irregular shapes microscopically (not shown). Also, breakdown of the red cell membrane as a permeability barrier was suggested by lack of lysis of modified red cells by hypotonic solutions.

Agglutination reactions are an imperfect means of assessing antigenic blockade as agglutination reactions may be influenced by factors such as changes in surface charge of red cells or shape of cells. For this reason, an independent means of measuring the blockade of a red cell antigen was employed. Red cells expressing the D antigen were modified by coupling with the bifunctional polyethylene glycol derivative. Modified cells and control cells were then incubated with antibody to the D antigen, and the amount of cell-bound antibody was measured by immunoassay. This analysis shown in TABLE II indicated a complete blockade (more than 99%) of antibody binding to the D antigen.

TABLE II

Blockade of D antigen by coupling of bis(propionyl-N-hydroxysuccinimide)-polyethylene glycol to red cells

| Red Cell Type | Molecules lgG/Cell |
|---|---|
| A, Rh Negative (negative control) | 396 |
| A, Rh Positive (positive control) | 11,233 |
| A, Rh Positive, polyethylene glycol-modified | 407 |

Modified and control cells were incubated with antibody to D antigen and the number of antibody molecules bound was measured by immunoassay. Rh negative cells lack D antigen and serve as a negative control.

EXAMPLE 4

Blockade of a variety of other antigens by attachment of polyethylene glycol to red cells was examined (TABLE III). Agglutination by antibodies to antigens of the Duffy (Fy), Kidd (Jk), Lewis (Le), and Rh groups (D) were inhibited as well as agglutination reactions by the lectins from *Dolichos bylorous* and *UIex europaens*. These results indicate a generalized blockade of red cell antigens. The antigens most resistant to blockade by red cell modifications with polyethylene glycol have been the A and B antigens, which probably reflects their high abundance, peripheral location, and carbohydrate nature (Walker, 1990).

TABLE III

Blockade of red cell antigens by coupling of bis(propionyl-N-hydroxysuccinimide)-polyethylene glycol

| | Agglutination Reaction | |
|---|---|---|
| Anfibody/Lectin | Untreated Cells | PEG-Red cells |
| Type $A_1$, Rh+ cells treated with 5% PEG derivative | | |
| Anti-D | 4+ | 0 |
| Anti-$Fy^b$ | 1+ | 0 |
| Anti-$Jk^a$ | 2+ | weak + |
| Anti-$Le^b$ | 2+ | 0 |
| Dolichos biflorous | 4+ | 0 |
| UIex europaeus | 4+ | 0 |

TABLE III-continued Blockade of red cell antigens by coupling of bis(propionyl-N-hydroxysuccinimide)-polyethylene glycol

| Antibody/Lectin | Agglutination Reaction | |
|---|---|---|
| | Untreated Cells | PEG-Red cells |
| Type A₁B cells treated with 25% PEG derivative | | |
| Anti-B | 4+ | 1+ |
| Anti~Jkb | 1+ | 0 |
| Anti~Leb | 3+ | 0 |

Blockade of antigens was assessed by inhibition of agglutination by antibodies and lectins versus specific antigens

EXAMPLE 5

Human serum has naturally-occurring antibodies to red cells of many species, such that xenotransfusion of red cells results in rapid agglutination or lysis of the cells by complement fixation. Blockade of porcine red cells by coupling of a polyethylene glycol derivative was examined for compatibility with human serum. Both agglutination and hemolytic actions of human serum were blocked by the modification of porcine red cells with polyethylene glycol.

TABLE IV

Blockade of porcine red cell antigens by propionyl-N-hydroxysuccinimide-methoxypolyethylene glycol (MW: 5,000)

| % PEG | Agglutination | Hemolysis |
|---|---|---|
| 0 | 4+ | Moderate |
| 5% | 3+ | Slight |
| 10% | 0 | None |
| 20% | 0 | None |
| 30% | 0 | None |
| 40% | 0 | None |
| 50% | 0 | None |

Modified porcine red cells were mixed with human serum and agglutination and lysis reactions were assessed.

EXAMPLE 6

Polyethylene glycol derivatives were purchased from Shearwater Polymers (Huntsville, Ala.). The 5% human albumin was purchased from American Red Cross Blood Services. Red cells were obtained from segments attached to units of donor red cells. Immucor (Norcross, Ga.) was the source of monoclonal/polyclonal anti-human globulin, antibodies to human red cell antigens. Agglutination reactions of red cells were assayed by standard tube techniques as described by the Technical Manual of for Blood Banks (Walker et al 1994).

Coupling of activated polyethylene glycols to red cells was conducted in 140 mM NaCl, 20 mM N-[2-hydroxyethyl)piperazine-N'[2-ethanesulfonic acid] (Hepes solution) adjusted to pH 9.0. Activated refers to polyethylene glycol which has chemically reactive esters attached. A 5% human albumin was mixed at room temperature with activated branched polyethylene glycol derivatives a 4 arm branched succinimidyl derivative of PEG propionic acid (SPA-PEG) a specific product thereof, i.e. 4 arm propionyl-N-hydroxysuccinimide-methoxypolyethylene glycol (MW 10,000) for one minute and then mixed with 5% suspension of red cells for 20 minutes and then fresh Hepes solution was added for developing polyethylene glycol-albumin copolymer layers for another 25 minutes. Cells were washed with PBS, pH 7.0 in a centrifugal cell washer before any analysis. The red cell survival studies were done using PKH-2 fluorescent dye technique as described by Read et al. in *Transfusion Journal* 31(6): 502–508, 1991.

EXAMPLE 7

Hemagglutination Tests

TABLE V shows that polyethylene glycol-albumin copolymers completely blocked all red cell antigen-antibody reactions except very weak microscopic agglutination with anti-A, anti-B and anti-A'B antibodies. Testing with polyclonal allo-antibodies such as anti-K, anti-FyA, anti-FyB, anti-JkA, anti-JkB, anti-S, anti-s and other Rh antibodies, showed same results as above which indicated a complete block of antigen-antibody reactions. Testing with anti-B and anti-A'B showed same results as above, negative on IS and 30'RT but micro + on anti-IgG phase.

TABLE V

Testing with polyclonal anti-D:

| | IS | 15'37C | anti-IgG |
|---|---|---|---|
| A+ untreated (control) | 4+ | | |
| A+ PEG-Albumin treated | 0 | 0 | 0 |
| A- untreated (control) | 0 | 0 | 0 |
| A- PEG-Albumin treated | 0 | 0 | 0 |

Testing with human polyclonal anti-A:

| | | | 30'37° C. | |
|---|---|---|---|---|
| | IS | 30'RT | anti-IgG | Titer at RT |
| A- untreated (control) | 4+ | 4+ | 4+ | 128 |
| A-PEG-Album. treated | 0 | 0 | micro + | |

Testing with monoclonal anti-A:

| | IS | 30'RT |
|---|---|---|
| A- untreated (control) | 4+ | 4+ |
| A- PEG-Albumin treated | 0 | micro + |

EXAMPLE 7

Red Cell Survival Studies

Figure 2:
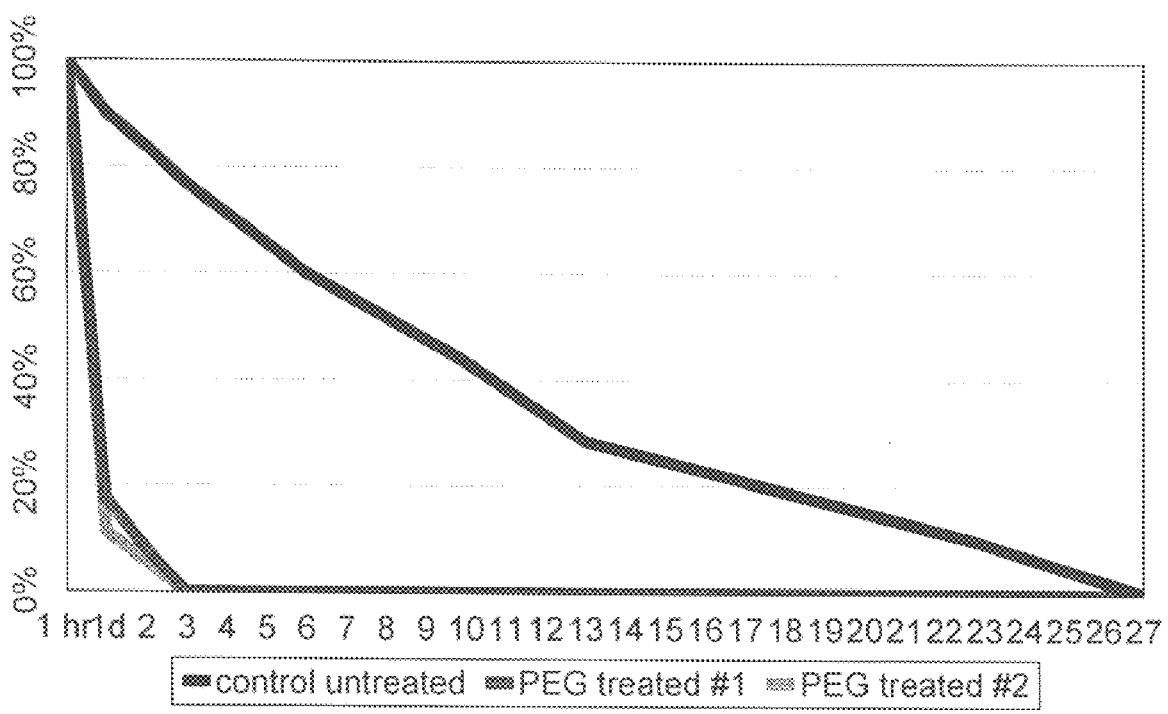
FIG. 2 shows the polyethylene glycol treated mouse red blood cells only had a 3 day life span. In contrast, untreated red blood cells had a 27 day life span.
Figure 3:
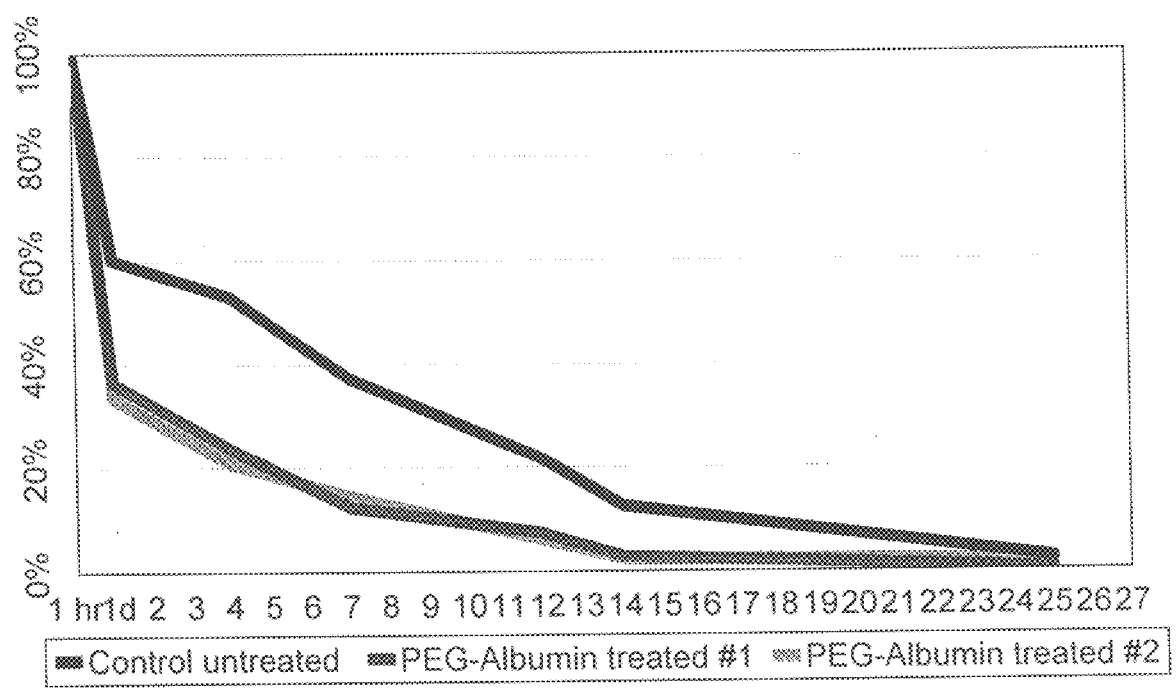
FIG. 3 shows the percentage of polyethylene glycol-albumin polymer-treated mouse red blood cells surviving over 27 days following incubation for 7 days.
Figure 4:
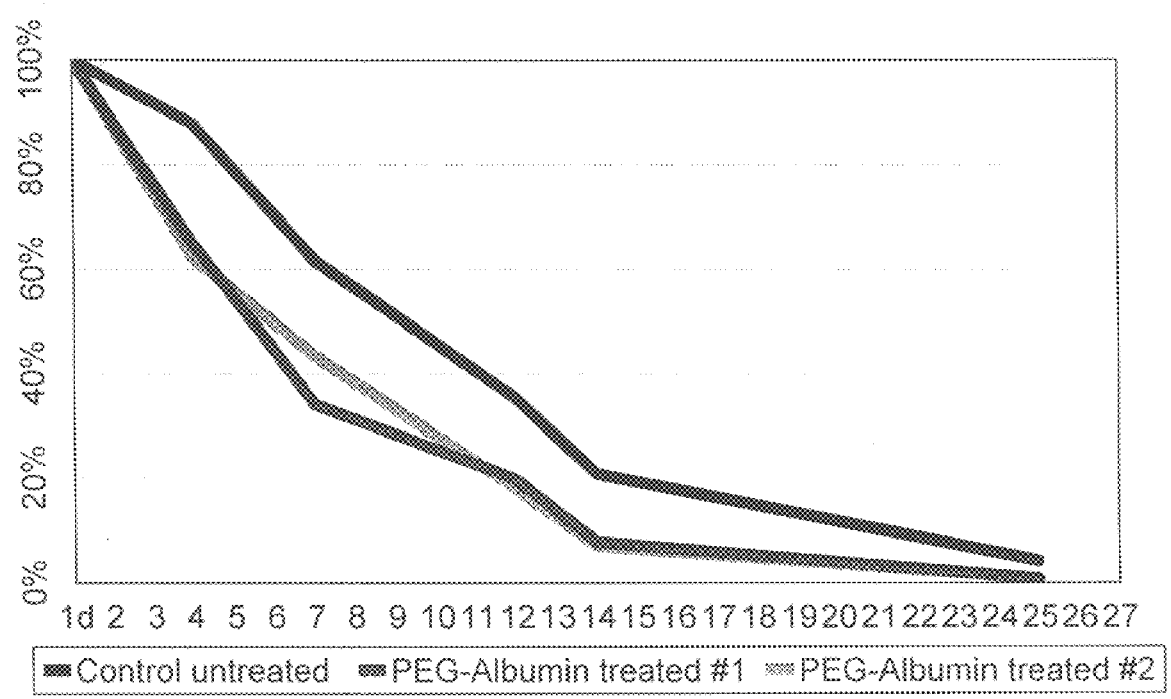
FIG. 4 shows the data shown in FIG. 3 except survival is shown as a percentage of cells surviving relative to those surviving at one day after transfusion (1d=100%).

The red cell survival studies showed polyethylene glycol-albumin treated mouse red blood cells have the same 27 days life span compared with untreated red blood cells (FIG. 1). In contrast, polyethylene glycol treated mouse red blood cells only have a 3 day life span (FIG. 2). Polyethylene glycol-albumin treated mouse red blood cells (in AS-5 additive solution, a solution containing dextrose, mannitol, adenine and sodium chloride that is used to preserve human red blood cells so that such cells can be stored for long periods of time) were stored in 4° C. refrigerator for one week. When transfused back into mouse, there was a loss of 60% of transfused red blood cells in first day and the remaining red cells had a 24 day life span. The untreated control mouse red cells showed loss of 40% of transfused red blood cells in first day and the remaining red cells have a 27 day life span (FIGS. 3 and 4). The AS-5 additive was not the optimal additive solution for mouse red cells, as it showed immediate large red cell destruction on both treated and untreated mouse red cells and a slight decrease of remaining red cell survival on polyethylene glycol-albumin treated compared with untreated mouse red cells.

EXAMPLE 8

Morphology of Red Blood Cells

Figure 5:
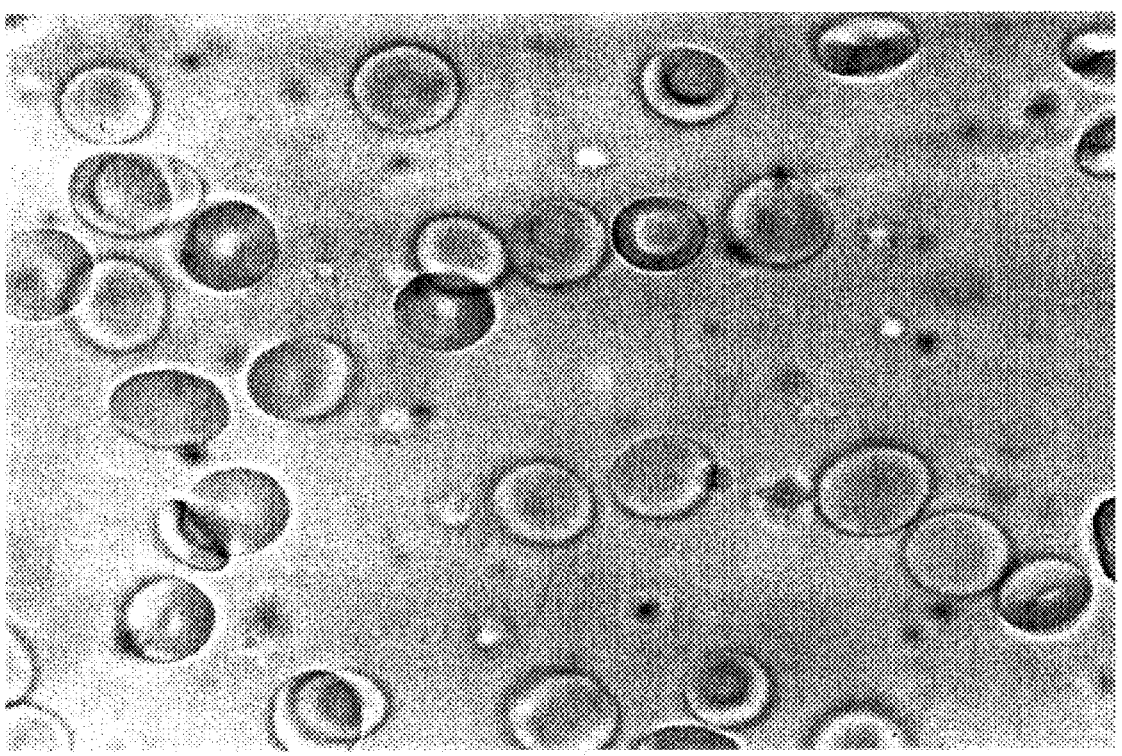
FIG. 5A shows the red cell morphology after polyethylene glycol-albumin copolymer treatment of human red blood cells in a wet preparation in normal saline (×700).
FIG. 5B shows control untreated human red blood cells
Figure 5:
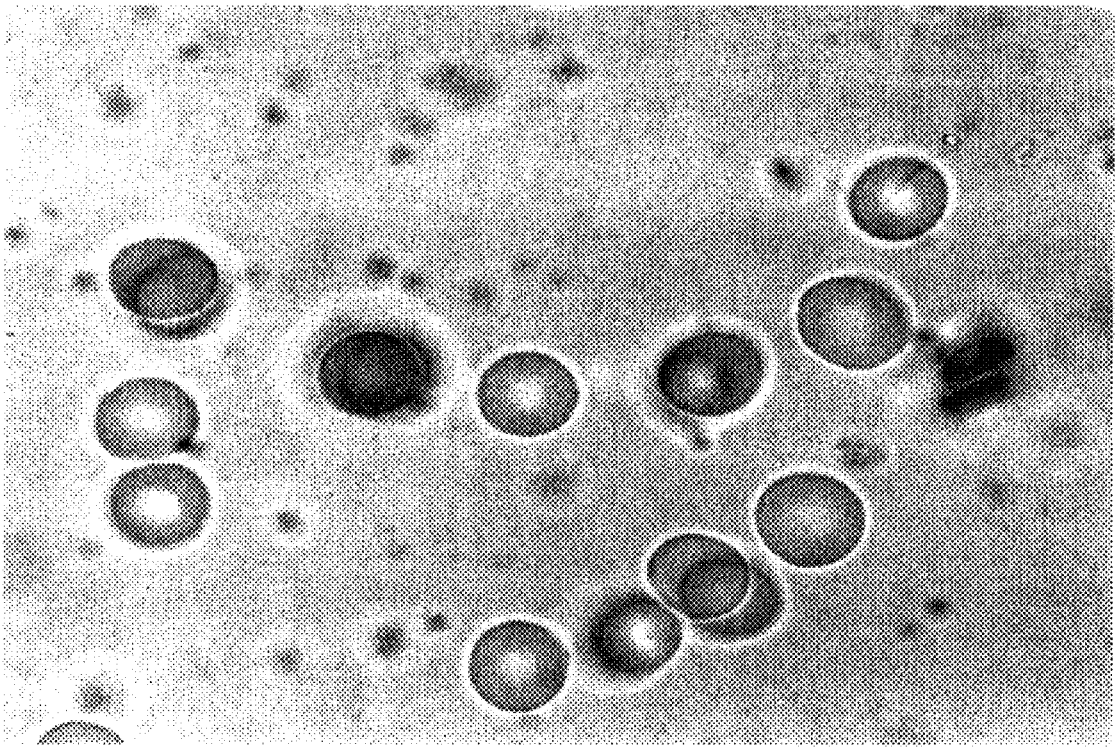

FIGS. 5A and 5B show that both polyethylene glycol-albumin treated and untreated control human red blood cells showed normal red cell morphology in microscopic examination.

The present invention showed that polyethylene glycol-albumin polymers are more efficient than polyethylene glycol polymer in covering the antigen sites on the red cell surface to prevent reactions with antibodies. Polyethylene glycol polymer is a single layer coated on the red cell surface, with space between each polymer which allows the antibody to reach the antigens. In contrast, the polyethylene glycol-albumin copolymers are multiple layers and have sheet-like structures due to cross-linked or branched polyethylene glycol and albumin polymers. These sheet-like structures prevent the antibody from reaching the antigens with the exception of ABO antibodies as ABO antigens extend out far from the surface. The polyethylene glycol-albumin copolymer had more efficient coverage on red cell surface and had less attached points on red cell surface which showed normal red cell morphology and red cell survival studies indicating very minimal damage to the red cell surface. The polyethylene glycol-albumin copolymers exhibit high potential as universal donor red cells for blood transfusion.

Thus, the present invention provides a composition of matter, comprising a red blood cell coated with a cross-linked or branched polyethylene glycol and albumin. Generally, any branched polyethylene glycol should be useful in creating the present compositions. Preferably, "arm" polyethylene glycols which have multiple molecules connnected together with multiple actives sites are preferred. For example, 1 arm refers to 1 PEG of a MW of about 3400–5000; 4 arm refers to 4 PEG molecules of about 15,000–20000 MW. Four PEGs connected together would have therefore 4 active sites.

Generally, the concentration of the polyethylene glycol is from about 0.5% to about 1% and the concentration of the albumin is from about 1.25% to about 10%. In a preferred form, the albumin is human albumin. In another aspect, the present invention can provide a white blood cell coated with a cross-linked mixture of branched polyethylene glycol and albumin so as to block the antigen sites on such a cell. For all of the compositions described herein, albumin may be preferred but other similar proteins could easily be used, e.g., fibrinogen.

Generally, in making the compositions described herein, the polyethylene glycol is mixed with the albumin to form a copolymer. Subsequently, the cells such as red blood cells are added. Over a short period of time, such as 20 minutes, the copolymer attaches to the red blood cell blocking the antigen sites. The cell is coated with polymeric mixture at least one time.

The present invention also provides a method of blocking blood group antigens on the surface of a red blood cell, comprising the step of contacting said cell with a pharmacologically effective concentration of the composition described herein.

The present invention is also directed to a composition of matter, comprising a red blood cell coated with a cross-linked or branched polyethylene glycol and branched polyethylene glycol amine.

The present invention is also directed to a composition of matter, comprising a red blood cell coated with a cross-linked or branched polyethylene glycol and an albumin-like compound, wherein said compound contains multiple reaction sites which form a cross-linked matrix with activated esters of polyethylene glycol.

The present invention is further directed to a composition of matter, comprising a cell coated with a cross-linked or branched polyethylene glycol and a protein. Preferably, the cell is a red or white blood cell but could be any cell type. In one embodiment, the protein is albumin but could be any protein containing multiple reaction sites which form a cross-linked matrix with polyethylene glycol. In a preferred embodiment, the polyethylene glycol is a branched polyethylene glycol.

EXAMPLE 9

Different kinds of branched amino-PEG (4 arm branched amino-PEG m.w. 10,000 and 2 arm branched amino-PEG m.w. 3,400 obtained from Shearwater) were also used to replace albumin. This data supports that any protein or compound containing multiple reaction sites with activated esters which form a cross-linked matrix (equivalent substitutes for albumin) can be used to create the universal donor blood cells of the present invention. Table I showed no differences using albumin or amino-PEG to conjugate with PEG on red blood cells to block antigen-antibody reactions.

TABLE VI

Testing with Monoclonal anti-D:

|  | IS | 15'37° C. | anti-IgG |
|---|---|---|---|
| A+ untreated (control) | 4+ | 4+ | 4+ |
| A–PEG-Albumin treated | 0 | 0 | 0 |
| A+ PEG-2 branched amino-PEG treated | 0 | 0 | 0 |
| A+ PEG-4 branched amino-PEG treated | 0 | 0 | 0 |
| A– untreated (control) | 0 | 0 | 0 |

Testing with polyclonal allo-antibodies such as anti-FyA, anti-FyB, anti-JkA, anti-JkB, anti-K, anti-S, anti-s and other Rh antibodies, showed the same results as above, which indicate a complete block of antigen-antibody reaction

TABLE VII

Testing with human polyclonal anti-A:

|  | IS | 30'RT | 30'37° C. anti-IgG | Titer at RT |
|---|---|---|---|---|
| A–untreated (control) | 4+ | 4+ | 4+ | 128 |
| A–PEG-Albumin treated | 0 | 0 | 0 (micro +) | |
| A+ PEG-2 branched amino-PEG treated | 0 | 0 | 0 (micro +) | |
| A+ PEG-4 branched amino-PEG treated | 0 | 0 | 0 (micro +) | |

Testing with anti-B and anti-A'B showed the same results as above, negative on IS and 30'RT, but microscopic + on anti-IgG phase.

In another study, human lymphocytes were treated with PEG-albumin copolymer in the same method used for red blood cells and then lymphocyte antigens (HLA antigens) were tested using standard microlymphocytotoxicity typing methods on pre- and post-treated lymphocyte suspension. The results are shown in Table VIII.

TABLE VIII

| HLA antigen specificity | HLA antibody number in tray | Reading Score*** Untreated | Reading Score*** PEG Treated** | 10 D* |
|---|---|---|---|---|
| A11 | 1F | 8 | 8 | 8 |
| A11 | 2F | 8 | 1 | 1 |
| A11 | 2E | 6 | 6 | 8 |
| A11 | 2D | 4 | 1 | 1 |
| A11 | 2C | 4 | 1 | 1 |
| A11 | 5D | 4 | 1 | 1 |
| A24 | 4B | 8 | 6 | 6 |
| A24 | 5A | 8 | 1 | 1 |
| A24 | 5B | 8 | 8 | 8 |
| B62 | 1E | 8 | 2 | 1 |
| B62 | 1F | 8 | 1 | 1 |
| B62 | 2F | 4 | 1 | 1 |
| B62 | 2E | 6 | 1 | 1 |
| B62 | 2A | 8 | 1 | 1 |
| B62 | 7D | 8 | 4 | 8 |
| B62 | 7E | 8 | 1 | 1 |
| BW4 | 10E | 6 | 1 | 1 |
| BW6 | 10D | 8 | 4 | 1 |
| BW6 | 10C | 8 | 2 | 1 |
| BW6 | 10B | 8 | 1 | 1 |
| BW6 | 10A | 8 | 8 | 8 |

*Lymphocytes treated with PEG-albumin copolymer and incubated in RPMI for 10 d.
**Lymphocytes (HLA typing: A11, A24, B62, BW4 & BW6) treated with PEG-albumin copolymer.
***Score 1 and 2 = negative reaction; 4 = weak reaction; 6 = moderate reaction; 8 = strong reaction The results contained in Tables VI, VII and VIII show that the PEG-albumin copolymer conjugated to lymphocyte surfaces could block or decrease exposure of antigens to most HLA antibodies. This blocking effect can continue at least 10 days. These results support that this method can not only block red cell surface antigens, but also block other cell's surface antigens from reacting to various antibodies.

REFERENCES

Fratantoni, J. (1991) Points to consider in the safety evaluation of hemoglobin-based oxygen carriers. Transfusion 3~:369–37~.

Griffiths, B., Cortes, A., Gilbert, N., Stevenson, P., MacDonald, S., Pepper, D. (1995) Haemoglobin-based blood substitutes and sepsis. Lancet 345:158–160.

Harris, J. M. 1992) Introduction to Biotechnical and Biomedical applications of poly(ethylene glycol), pp.1–14 in Poly(Ethylene Glycol) Chemistry, Ed.: 3. M. Harris, Plenum Publishing, New York, N.Y.

Issitt P. D. (1985) Applied Blood Group Serology, Montgomery Scientific Publications, Miami, Fla.

LoBuglio, A. F., Court, W. S., Vinocur, L., Maglon, O., Shaw, G. M. (1983) Immune thrombocytopenic purpura. Use of $I^{125}$-labeled antihuman IgG monoclonal antibody to quantify platelet-bound IgG. New Engl. J. Med. 309:459–463.

Mollison, P. L., Engelfriet C. P., Contreras M. (1987) Blood Transjitsion in Clinical Medicine (Blackwell Scientific Publications, Oxford, ed. 8,1987), pp.195–636.

Walker, R. H. (1990) Technical Manual, 10th Edition, American Association of Blood Banks, Arlington, Va.

Zalipsky, S. and Lee, C. (1992) Use of functionalized poly(ethylene glycol)s for modification of polypeptides, pp.347–370, in Poly(ethylene Glycol) Chemistry, Ed.: J. M. Harris, Plenum Publishing, New York, N.Y.

Read, E. J., Cardine, L. L., Yu, M. Y. (1991) Flow cytometric detection of human red cells labeled with a fluorescent membrane label: potential application to in vivo survival studies. Transfusion 31(6): 502–508

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition of matter, comprising a red blood cell coated with a cross-linked or branched polyethylene glycol and albumin.

2. The composition of claim 1, wherein said branched polyethylene glycol is an arm polyethylene glycol.

3. The composition of claim 2, wherein said arm polyethylene glycol is a 4 arm polyethylene glycol.

4. The composition of claim 3, wherein said arm polyethylene glycol is 4 arm propionyl-N-hydroxysuccinimide-methoxypolyethylene glycol.

5. The composition of claim 1, wherein the concentration of said polyethylene glycol is from about 0.5% to about 1%.

6. The composition of claim 1, wherein the concentration of said albumin is from about 1.25% to about 10%.

7. The composition of claim 1, wherein said albumin is human albumin.

8. The composition of claim 1, wherein the cell is coated with cross-linked or branched polyethylene glycol and albumin at least one time.

9. A method of blocking blood group antigens on the surface of a red blood cell, comprising the step of coating said cell with a pharmacologically effective concentration of a cross-linked or branched polyethylene glycol and albumin.

10. The method of claim 9, wherein the concentration of said polyethylene glycol is from about 0.5% to about 1%.

11. The method of claim 9, wherein the concentration of said albumin is from about 1.25% to about 10%.

12. The method of claim 9, wherein said albumin is human albumin.

13. A composition of matter, comprising a red blood cell coated with a cross-linked or branched polyethylene glycol and branched polyethylene glycol amine.

14. A composition of matter, comprising a red blood cell coated with a cross-linked or branched polyethylene glycol and a compound containing multiple reaction sites which form a cross-linked matrix with activated esters of polyethylene glycol.

15. A composition of matter, comprising a cell coated with a cross-linked or branched polyethylene glycol and a protein.

16. The composition of claim 15, wherein said cell is a red blood cell.

17. The composition of claim 15, wherein said protein is albumin.

18. The composition of claim 15, wherein said polyethylene glycol is a branched polyethylene glycol.

19. The composition of claim 15, wherein said protein contains multiple reaction sites which form a cross-linked matrix with of polyethylene glycol.

* * * * *